United States Patent
King

(10) Patent No.: US 10,602,917 B2
(45) Date of Patent: Mar. 31, 2020

(54) SWITCHING BETWEEN WHITE LIGHT IMAGING AND EXCITATION LIGHT IMAGING LEAVING LAST VIDEO FRAME DISPLAYED

(71) Applicant: Karl Storz Imaging, Inc., Goleta, CA (US)

(72) Inventor: Timothy King, Goleta, CA (US)

(73) Assignee: Karl Storz Imaging, Inc., Goleta, CA (US)

( * ) Notice: Subject to any disclaimer, the term of this patent is extended or adjusted under 35 U.S.C. 154(b) by 1015 days.

(21) Appl. No.: 14/145,620

(22) Filed: Dec. 31, 2013

(65) Prior Publication Data

US 2015/0182106 A1    Jul. 2, 2015

(51) Int. Cl.
*A61B 1/04* (2006.01)
*A61B 5/00* (2006.01)
*A61B 1/00* (2006.01)

(52) U.S. Cl.
CPC ............ *A61B 1/043* (2013.01); *A61B 1/0005* (2013.01); *A61B 5/7425* (2013.01); *A61B 5/0071* (2013.01); *A61B 5/0084* (2013.01)

(58) Field of Classification Search
CPC ... A61B 1/043; A61B 1/0638; A61B 1/00009; A61B 1/0005; A61B 1/0676; A61B 5/0071; A61B 5/0084; A61B 18/20; A61B 8/12; A61B 10/04
See application file for complete search history.

(56) References Cited

U.S. PATENT DOCUMENTS

| | | | |
|---|---|---|---|
| 4,556,057 A | 12/1985 | Hiruma et al. |
| 4,699,125 A | 10/1987 | Komatsu |
| 4,768,513 A | 9/1988 | Suzuki |
| 4,821,117 A | 4/1989 | Sekiguchi |
| 4,885,634 A | 12/1989 | Yabe |

(Continued)

FOREIGN PATENT DOCUMENTS

EP    1743568 A2    1/2007

OTHER PUBLICATIONS

European Search Report Application No. EP 14 19 9614 Completed: May 19, 2015; dated May 29, 2015 6 pages.

*Primary Examiner* — Baisakhi Roy
*Assistant Examiner* — Jason M Ip
(74) *Attorney, Agent, or Firm* — Whitmyer IP Group LLC

(57) ABSTRACT

Still image display of a recent video image of tissue as a reference still image prior to a switch in the mode of illumination of the tissue. The still image is displayed concurrently with live video of the tissue under a different mode of illumination, to facilitate discrimination between healthy and diseased tissue, and further facilitate therapeutic intervention. The reference still image may be displayed either as an insert (picture-in-picture), side-by-side, or the like concurrently with the live video image. In some embodiments, when a practitioner switches a light source from "excitation-light" to "white light", the "excitation-light" video may be frozen/captured and displayed as a reference still image as a PIP, and the "white-light" live video is displayed concurrently. When the source is switched again, the "white-light" video may be frozen/captured and displayed as a reference still image, and the "excitation-light" live video is displayed concurrently.

12 Claims, 4 Drawing Sheets

(56) References Cited

U.S. PATENT DOCUMENTS

| | | |
|---|---|---|
| 4,930,516 A | 6/1990 | Alfano et al. |
| 5,034,888 A | 7/1991 | Uehara et al. |
| 5,507,287 A | 4/1996 | Palcic et al. |
| 5,590,660 A | 1/1997 | MacAulay et al. |
| 5,646,680 A | 7/1997 | Yajima |
| 5,647,368 A | 7/1997 | Zeng et al. |
| 5,749,830 A | 5/1998 | Kaneko et al. |
| 5,827,190 A | 10/1998 | Palcic et al. |
| 5,986,271 A | 11/1999 | Lazarev et al. |
| 6,028,622 A | 2/2000 | Suzuki |
| 6,192,267 B1 | 2/2001 | Scherninski et al. |
| 6,293,911 B1 | 9/2001 | Imaizumi et al. |
| 6,364,829 B1 | 4/2002 | Fulghum |
| 6,422,994 B1 | 7/2002 | Kaneko et al. |
| 6,603,552 B1 | 8/2003 | Cline et al. |
| 6,899,675 B2 | 5/2005 | Cline et al. |
| 7,420,151 B2 | 9/2008 | Fengler et al. |
| 7,965,878 B2 | 6/2011 | Higuchi et al. |
| 2001/0027475 A1* | 10/2001 | Givol ............... H04L 29/06027 709/204 |
| 2002/0087047 A1 | 7/2002 | Remijan et al. |
| 2005/0288556 A1 | 12/2005 | Sugimoto |
| 2006/0173240 A1* | 8/2006 | Fukuyama ......... A61B 1/00039 600/118 |
| 2006/0256191 A1* | 11/2006 | Iketani et al. .................. 348/65 |
| 2011/0287387 A1 | 11/2011 | Chen et al. |

* cited by examiner

SWITCHING BETWEEN WHITE LIGHT IMAGING AND EXCITATION LIGHT IMAGING LEAVING LAST VIDEO FRAME DISPLAYED

FIELD OF THE INVENTION

The invention relates to diagnostic imaging techniques generally, and more specifically to automatically displaying the last live video image of tissue prior to a switch in the mode of illumination as a reference still image. The reference still image is displayed concurrently with a live video image of the tissue under a different mode of illumination to facilitate discrimination between healthy and diseased tissue and to further facilitate therapeutic intervention.

BACKGROUND OF THE INVENTION

Recently, diagnostic endoscopic techniques have been developed to irradiate tissue to be studied with visible light and to detect resulting fluorescent images which are then analyzed for diagnostic purposes. These techniques have been found particularly useful for diagnosing disease conditions such as cancers or tissue degeneration and for highlighting the boundary regions of such conditions under study. These techniques are sometimes enhanced by also studying normal light images resulting from reflection of the irradiating visible light (usually white light).

In the case of autofluorescence, i.e., the stimulated emission resulting from impingement of the excitation light onto a biological tissue, the fluorescence typically has a longer wavelength than that of the excitation light. Fluorescent substances within organisms are exemplified by collagens, NADH (nicotinamide adenine dinucleotide), FMN (flavin mononucleotide), pyridine nucleotide and the like. Recently, the relationship between such fluorescent substances and various diseases has been recognized, making it possible to diagnose cancers and the like by use of these fluorescences.

In addition, certain fluorescent substances such as HpD (hematoporphyrin), Photofrin, ALA (delta-amino levulinic acid), and GFP (Green fluorescent protein), are selectively absorbed by cancers and thus may be used as contrast materials. In addition, certain fluorescent substances may be added to a monoclonal antibody whereby the fluorescent may be attached to affected areas by an antigen antibody reaction.

Lasers, mercury lamps, metal halide lamps, xenon lamps, and the like may be used as and for the excitation light, which may be of a certain frequency or frequencies or may cover a certain spectrum that is useful for Autofluorescence ("AF"), Photodynamic Diagnosis ("PDD"), Indocyanine green ("ICG"), or other such known diagnostic techniques. For example, when a light with the wavelength of 437 nm is emitted onto a gastrointestinal tract tissue, green autofluorescence by abnormal tissues is attenuated compared to the autofluorescence of normal tissues, but red autofluorescence of abnormal tissues is not attenuated as much compared to the autofluorescence of normal tissues.

Since the fluorescent images obtained in this way typically have very low reflective intensities as compared to the reflected images obtained with conventional white light, photomultiplication, such as by using a higher camera system gain factor or increased imager integration time, may be necessary.

Generally, when a blue or ultraviolet light is emitted onto biological tissue, an autofluorescence occurs within a longer wavelength band than that of the excitation light. Moreover, fluorescent spectra are different between normal tissues and abnormal tissues, such as precancerous tissues, cancerous tissues, inflammatory tissues and dysplastic tissues, such that the existence of lesions and conditions of lesions can be detected based on subtle changes in coloration of the fluorescent images.

In particular, since with a blue excitation light, the intensity distribution of fluorescence stimulated near the green region (especially that of 490 nm-560 nm) is stronger in normal tissue than in diseased tissue, emissions in the green region and in the red region (e.g., wavelengths in the 620 nm-800 nm region) are arithmetically processed to generate two-dimensional fluorescent images, and by these fluorescent images the discrimination between abnormal and/or diseased areas and normal areas can be achieved.

In known systems, video images are produced for diagnostic observation of autofluorescent emissions, and adjustments are made to the ratio between the video signals corresponding to the green and red fluorescent intensities to allow normal tissues to have a certain color tone. Accordingly, tissue known to be normal is first observed, and the ratios of the red and green emissions are adjusted to establish a reference color tone. Then, after the adjustment of the color tone of the normal parts, the potentially diseased tissue is observed. In this way, the normal parts are designated with a certain color tone and abnormal parts are designated with different color tones from that of the normal parts due to the attenuation of the green signal. By the differences in color tones between abnormal and normal parts, the abnormal parts can be visualized. Typically, the ratio is adjusted so that the normal tissue appears in a cyanic color tone and diseased tissue appears as a red color tone.

Moreover, in some fluorescent observation devices, a single light source is used both as an excitation light to conduct fluorescent observations and as a white light to conduct white light observations by insertion and removal of a color filter, either by mechanical or electronic means. As will be understood, when only fluorescent images are desired, there should be no illumination by, or detection of, white light, but only illumination by and detection of the excitation light. Thus, switching is required so that when a white light image is to be obtained, a white light is emitted and/or detected, and when a fluorescent image is to be obtained, an excitation light is emitted and/or detected.

Further, image switching is typically controlled so that when white light is emitted the resulting image is provided only to a white image imaging device, and so that when the excitation light is emitted, the fluorescent image is provided only to a high-sensitivity fluorescent imaging device.

Generally, since the subtle variations in coloration of fluorescent images are subjectively visualized by a medical practitioner, the lack of fixed discrimination standards makes it difficult to compare findings by different practitioners, and at different medical facilities.

Also, because adjustment of color tone for normal tissue is conventionally performed and dependent upon the individual judgment of the medical practitioner, the absence of fixed calibration standards renders objective diagnosis by color tone difficult if not impossible. Resultantly, comparison of the white light image against the excitation light image may be the most accurate means to discriminate diseased from healthy tissue. To accomplish this discrimination, switching back-and-forth between white light and excitation light images is advantageous. The switching becomes more critical in a therapeutic environment. If diseased tissue is discovered, the medical practitioner may need to excise the tissue while switching between the two images to ensure all diseased tissue has been removed.

Further, due to conventional fluorescence diagnosis endoscope system construction described above, only the light produced by the fluorescence of tissue is detected by the imager element of the endoscope. Thus, suspect tissue cannot be observed when illuminated with white light by the same endoscope. In some instances, to examine suspect tissue using white light, the endoscope designed for fluorescence diagnosis is removed and another endoscope for normal observation is inserted. This is time consuming, disruptive, and potentially hazardous to a patient during an examination and/or surgical procedure.

Various display schemes relating to differentiating normal tissue from diseased tissue are known. Generally, these display schemes fall into 4 categories:

1. Diseased tissue view and normal tissue view displayed combined/superimposed within a single video frame.
2. Diseased tissue view and normal tissue view displayed combined/superimposed with alternating video frames.
3. Diseased tissue view and normal tissue view displayed separately within a single video frames.
4. Diseased tissue view and normal tissue view displayed separately within alternating video frames.

Depending upon how the excitation-light is generated and/or detected, this switching requires that a light source switch between a "white-light" mode and "excitation light" mode, and can be initiated from the CCU (from a camera head button, for example).

Regardless of how the excitation light image is produced, either superimposing the excitation light image over the white light image, or a side-by-side composite image, is typical. For example:

U.S. Pat. No. 4,556,057 to Hiruma et al. relates to a cancer diagnosis device which selectively illuminates a cancer focus with white light and laser light synchronously with an imaging device, images of which are coupled to a spectroscope for detecting spectral response.

U.S. Pat. No. 4,699,125 to Komatsu relates to storing superposed frames from an endoscopic video in response to a freeze instruction, photographing a frozen image displayed on a display means, and sequentially comparing image signals for a predetermined color component in order to obtain a clear frozen image through motion detection.

U.S. Pat. No. 4,768,513 to Suzuki relates to analyzing fluorescence wavelength patterns for diagnostic purposes.

U.S. Pat. No. 4,791,480 to Muranaka relates to an endoscope having an adjustable light source which can be used to produce video and still images. When a still image is taken, the illuminating light can be pulsed during frame transfer from the solid state camera element in order to avoid producing a blurred image.

U.S. Pat. No. 4,821,117 to Sekiguchi relates to alternately irradiating an object with visible and excitation radiation and controlling the irradiating, storage, and displaying means to simultaneously display a visible radiation image and a fluorescent image.

U.S. Pat. No. 4,885,634 to Yabe relates to simultaneously displaying a color image and a specific wavelength image on separate monitors or on the same monitor screen.

U.S. Pat. No. 4,930,516 to Alfano et al. relates to exciting a tissue with monochromatic lights and measuring the intensity of visible native luminescence emitted from the tissue of at least two wavelengths, and displaying a signal corresponding to the ration between the intensities of at least two wavelengths.

U.S. Pat. No. 5,034,888 to Uehara et al. relates to an electronic endoscope apparatus having different image processing characteristics for a moving image and a still image.

U.S. Pat. No. 5,507,287 to Palcic et al. relates to sending first and second spectral band autofluorescence images to the red and green channels of an RGB video monitor to create a combined display image.

U.S. Pat. No. 5,590,660 to MacAulay et al. relates to sending autofluorescence and remittance light images to the red and green channels of an RGB video monitor to create a pseudo-color image.

U.S. Pat. No. 5,646,680 to Yajima relates to displaying either an endoscope video signal either through a peripheral device or directly so that the peripheral device can be bypassed in case of a malfunction.

U.S. Pat. No. 5,647,368 to Zeng et al. relates to collecting color filtered excitation light and autofluorescence light and sending the images to the red and green channels of an RGB video monitor to create a false color contrast image.

U.S. Pat. No. 5,749,830 to Kaneko et al. relates to switching display between simultaneous display and time-divided display of normal observation video and fluorescent observation video.

U.S. Pat. No. 5,827,190 to Palcic et al. relates to storing and combining sequential autofluorescence and reflectance images for simultaneous display as a pseudo-color image.

U.S. Pat. No. 5,986,271 to Lazarev et al. relates to displaying a superimposed or first and second region view of both a full color and resulting autofluorescence image.

U.S. Pat. No. 6,028,622 to Suzuki relates to displaying superimposed fluorescent images under different excitation lights.

U.S. Pat. No. 6,099,466 to Sano et al. relates to displaying a color image and/or a fluorescence image produced by processing fluorescence filtered image signals.

U.S. Pat. No. 6,192,267 to Scherninski et al. relates to an angiography device for displaying contrast enhanced fluorescence images.

U.S. Pat. No. 6,293,911 to Imaizumi et al. relates to simultaneously displaying an image under autofluorescence and white light in superimposed or side-by-side format, and where a second image signal can be subtracted from a first image signal.

U.S. Pat. No. 6,364,829 to Fulghum relates to display of sequentially or simultaneously detected fluorescence and reference images.

U.S. Pat. No. 6,422,994 to Kaneko et al. relates to superimposing a tissue fluorescence image color interpretation guide and an enhanced fluorescence image video.

U.S. Pat. No. 6,603,552 to Cline et al. relates to superimposing reflected light and fluorescence images.

U.S. Pat. No. 6,899,675 to Cline et al. relates to displaying superimposed video images from pixels of a low light color image sensor having one or more color filters.

U.S. Pat. No. 7,420,151 to Fengler et al. relates to simultaneously displaying a white light and short-wavelength light image.

U.S. Pat. No. 7,965,878 to Higuchi et al. relates to an endoscopic system that stores matrix data for forming a spectral image and forms a spectral image in a selected wavelength band according to a matrix operation on an original still image. The original still and one or more spectral images can then be displayed.

However the use of video having superimposed, interleaved, or side-by-side diagnostic and normal views as described above can be confusing and lack clarity in many circumstances.

It is therefore desired to provide a device which addresses these deficiencies.

SUMMARY OF THE INVENTION

Accordingly, it is an object of the present invention to provide a still image of tissue under a particular type of illumination concurrently with a video image of the tissue under a different type of illumination.

This and other objects are achieved by providing an imaging system which includes an endoscope; a first source for providing illumination with a first light; a second source for providing illumination with a second light; an imager for capturing video from the endoscope; a first display area for displaying a live video image; and a second display area for displaying a still image taken from the live video image prior to a change between illumination with the first light and illumination with the second light.

In some embodiments, the first and second sources comprise a single device which can switch between the first and second lights.

In some embodiments, the first and second sources comprise different devices.

In some embodiments, the second display area is at least partially within the first display area.

In some embodiments, the first display area and the second display area are located on the same display device.

In some embodiments, the first light comprises visible light.

In some embodiments, the second light comprises an excitation light. The excitation light may include at least one wavelength which can activate a fluorescent or photodiagnostic substance.

In some embodiments, the second light comprises non-visible light.

Other objects of the present invention are achieved by providing an imaging system which includes an endoscope; a first source for irradiating an object with a first light; a second source for irradiating an object with a second light; an imager for capturing a video image from the endoscope; a first display for displaying the video image during irradiation with the first light; and, a second display for displaying a still image taken during irradiation with the second light.

Further objects of the present invention are achieved by providing an imaging system which includes a control unit for receiving image information from an endoscope that relates to an object, which can transmit for display on a first display area a video image of the object, and which can transmit for display on a second display area concurrently with the video image a still image of the object taken prior to a change in a wavelength of illumination of the object.

Still, further objects of the present invention are achieved by providing a system for photodynamic diagnosis which includes a first source for providing illumination at a photodynamic wavelength; a second source for providing illumination at a non-photodynamic wavelength; an imager for capturing video of tissue illuminated by the first source or the second source; a first display area for displaying the video image during illumination at the first wavelength; and, a second display area for displaying a still image taken from the video image during illumination at the second wavelength.

In some embodiments, the first and second sources comprise a single device which can switch between the first and second wavelength.

In some embodiments, the first and second sources are provided by different devices.

In some embodiments, the first display area and the second display area overlap.

In some embodiments, the first display area and the second display area are located on the same display device.

In some embodiments, the first wavelength comprises visible light.

In some embodiments, the second wavelength comprises excitation light. The excitation light may include at least one wavelength which can activate a fluorescent substance.

In some embodiments, the second wavelength comprises non-visible light.

Still further objects of the present invention are achieved by providing a method for creating a reference image during diagnostic imaging which includes selectively irradiating an object with a first light and a second light; displaying a video image of the object; capturing a still image of the object immediately prior to switching between irradiating the object with the first and second light; and, displaying the still image concurrently with the video image.

In some embodiments, the first light is visible light.

In some embodiments, the second light is diagnostic light.

In some embodiments, the still image is displayed picture-in-picture with the video image.

In various embodiments, the diagnostic light produces auto-fluorescence in a tissue and/or causes a drug to fluoresce.

In some embodiments, the both the first light and second light are diagnostic lights. Other objects of the invention and its particular features and advantages will become more apparent from consideration of the following drawings and accompanying detailed description.

DETAILED DESCRIPTION OF THE INVENTION

The instant invention provides a recent "opposite mode" reference still image from the mode currently provided by live video, and displays the "opposite mode" reference still image on the monitor either as an insert (picture-in-picture, PIP), side-by-side, or the like concurrently with the live video image.

For example, when a practitioner switches the light source from "excitation-light" to "white light", the "excitation-light" video may be frozen/captured and displayed as a reference still image as a PIP, and the "white-light" live video displayed as the primary video image.

Conversely, when the practitioner switches the light source from "white-light" to "excitation light", the "white-light" video may be frozen/captured and displayed as a reference still image as a PIP, and the "excitation-light" live video displayed as the primary video image.

It should be understood that while white light and excitation light are used as general terms for the sake of example herein, the invention is not limited to these particular forms of light. For example, the system may switch between two distinct kinds of diagnostic light, between two distinct kinds of non-diagnostic light, or among a greater number of diagnostic and non-diagnostic light. Also, the term light is used from time to time herein with respect to diagnostic illumination, however it is understood that in some embodiments light may include either visible or non-visible wavelengths of electromagnetic radiation and/or photonic energy.

Figure 1:
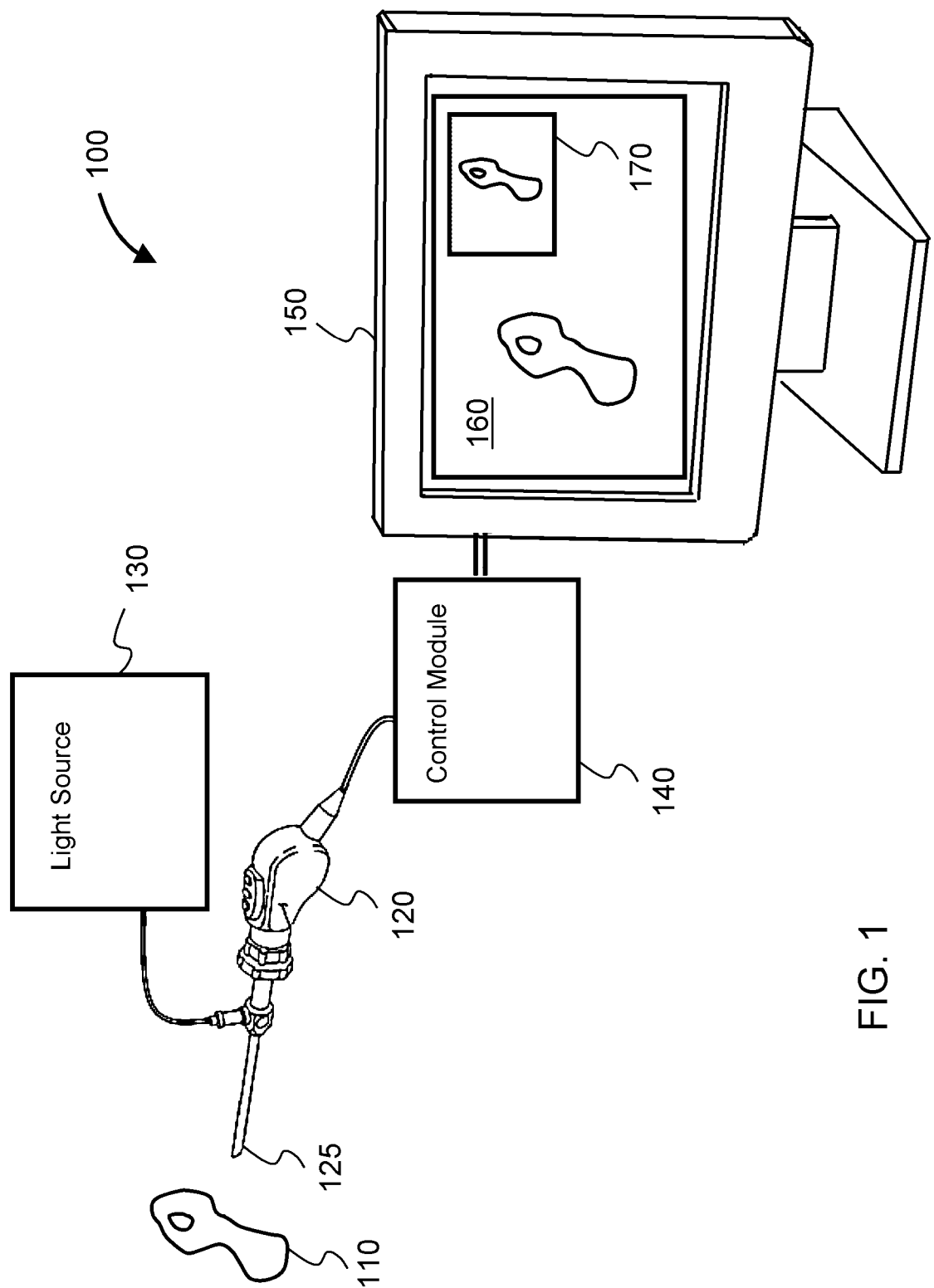
FIG. 1 is a block diagram showing an example system according to aspects of the invention.

FIG. 1 shows an example system 100 according to aspects of the invention.

Example system 100 is an endoscopic system configured for diagnosing diseased tissue 110. System 100 includes an endoscope with endoscopic camera 120, light source 130, control module 140, and display 150.

Endoscopic camera 120 is shown as detachable from the endoscope, the endoscope being configured to emit light supplied by light source 130 from the endoscope distal end 125 for illuminating diseased tissue 110. The light may be transmitted to the endoscope distal end 125 via one or more optical fibers, or by other known methods.

Although endoscopic camera 120 is described as detachable from the endoscope in this example, other imaging devices can be used without departing from the invention, such as video endoscopes, flexible endoscopes, variable direction-of-view endoscopes, solid state variable direction-of-view endoscopes, and the like.

Light source 130 provides light to the endoscope distal end 125 for illuminating tissue 110. Light source 130 is capable of producing two or more types of light. For example, light source 130 may supply white light, ultraviolet light, or other types of light, either concurrently or alternately, to the endoscope distal end 125 for illuminating tissue 110.

Although light source 130 is shown as a discrete module in system 100, in alternative embodiments, light source 130 may be integrated into the endoscope or control module 140, for example. Light source 130 may also be implemented as two or more separate modules, each supplying light of different wavelengths, for example. Various permutations on these arrangements that do not depart from the invention will be evident to those having skill in the art. Light source 130 may be comprised of one or more lamps, light-emitting diodes ("LEDs") or other solid state light sources, lasers, or other suitable light sources. The light produced by light source 130 typically will be switchable between a white light and a diagnostic light having a wavelength(s) or spectrum optimized for producing fluorescence or other contrast effects in tissue under observation.

Under illumination by light from light source 130, tissue 110 reflects and/or emits light in response depending upon the wavelengths of the light. Endoscopic camera 120 receives the reflected and/or emitted light from tissue 110. The emitted light may include light emitted by biological structures through auto-fluorescence, light produced by the stimulated fluorescence of drugs administered to tissue 110, other known types of light emissions, or several or all of these simultaneously.

Endoscopic camera 120 receives the light reflected and/or emitted from tissue 110 and generates one or more image signals based on the light received from tissue 110. The image signals are transmitted by endoscopic camera 120 to the control module 140.

Control module 140 may be a camera head module, camera control unit, or other imaging device, image receiving device, or other device that receives image data from endoscopic camera 120 and processes it for display.

Control module 140 may also be in communication with light source 130 in order to control its operation or to receive signals from light source 130 as to its status or mode of operation. For example, light source 130 may in some embodiments provide information to control module 140 as to whether it is supplying white or diagnostic light to endoscopic camera 120, for example, or may indicate that the mode has changed or toggled, or may indicate its mode from among a number of illumination modes and/or types. In some embodiments, light source 130 may receive a command from control module 140 to change its mode of operation from white to diagnostic light, or from diagnostic to white light, for example. In still another embodiment, both the light source 130 and control module 140 may receive a light mode change signal from a common source, such as from a button on an endoscope or other instrument, for example. Communication between control module 140 may take place via any known means, such as through a common signal connection with endoscopic camera 120 or a separate signal connection, for example, to provide information about the light emitted by light source 130 to control module 140.

Control module 140 transmits a video image 160 to display 150 that is produced by processing image data received from endoscopic camera 120. For example, image 160 may be a video image of tissue 110 as illuminated by a white light supplied by light source 130.

Control module 140 is also configured such that it can transmit a still image 170 to display 150 for display concurrently with video image 160.

When the mode of operation of light source 130 is switched, such that it supplies diagnostic light to endoscopic camera 120 and stops supplying white light, for example, control module 140 transmits a still image 170 to display 150 which shows the last frame of the video image 160 taken under the previous mode of operation (in this case, under white light). Control module 140 continues to transmit this still image 170 for display on display 150 while concurrently transmitting video image 160 for display on display 150. Thus in this scenario, image 170 shows the last frame of video of tissue 110 that was taken while light source 130 was supplying white light, while image 160 displays a live video image of tissue 110 while it is being illuminated with diagnostic light by light source 130.

Because non-fluorescing structures may not be as distinct under diagnostic light, providing a still reference image of tissue 110 illuminated under ordinary white light while showing live video of tissue 110 under diagnostic light has the advantage of assisting a surgeon to navigate such structures.

It should be noted that although image 170 has been described as showing the last frame of video 160 taken in the previous mode of operation of light source 130, it is understood that a different frame of video could be substituted in some embodiments without departing from the invention. For example, in some embodiments, image 170 may show a recent frame of such video that is not precisely the last frame, without departing from the invention. This may be done, for example, to compensate for processing delays within control module 140 if necessary. Furthermore, while still image 170 is shown inset or overlapping video image 160 in a picture-in-picture ("PIP") type display, in various embodiments these images can be reversed such that the video image is inset, or such that images 160, 170 may be shown side-by-side or otherwise arranged separately on display 150. Images 160, 170 may also be displayed on separate monitors in some embodiments.

If the mode of operation of light source 130 is subsequently switched, such that it supplies white light to endoscope 120 and stops supplying diagnostic light for example, control module 140 transmits an updated still image 170 to display 150 which shows the last frame of the video image 160 taken under the previous mode of operation (in this case, under diagnostic light). Control module 140 continues to transmit this updated still image 170 for display on display 150 while concurrently transmitting video image 160 for display on display 150. Thus in this scenario, image 170 will show the last frame of video of tissue 110 that was taken while light source 130 was supplying diagnostic light, while image 160 displays a live video image of tissue 110 while it is being illuminated with white light by light source 130.

Displaying the last live video image as a reference still image concurrently with current live video image in this way can also have the advantage of facilitating discrimination between healthy and diseased tissue, and further facilitate therapeutic intervention.

Furthermore, using an updated still reference image for comparison with a video image can also have the advantage of reducing task overload by retaining a fixed familiar reference, while still being able to update the reference image on demand when and as required. Updating a still reference image for comparison with a live video image in this way can provide for improved situational awareness in critical medical procedures where the angle or orientation of view may be changed one or more times.

It should be noted that in some embodiments where light source 130 has more than two modes of operation, control module 140 may be configured to cycle images 160 and 170 with each mode change, such that video image 160 shows live video taken under the current illumination mode and still image 170 shows the last frame of the video taken under the most recent mode. Because different biological structures and marking or fluorescence substances may respond differently to stimulation by different wavelengths of diagnostic (or white) light, this can have the advantage of allowing a surgeon to select from among a number of diagnostic wavelengths to provide the most useful reference and video images, for example.

Figure 2:
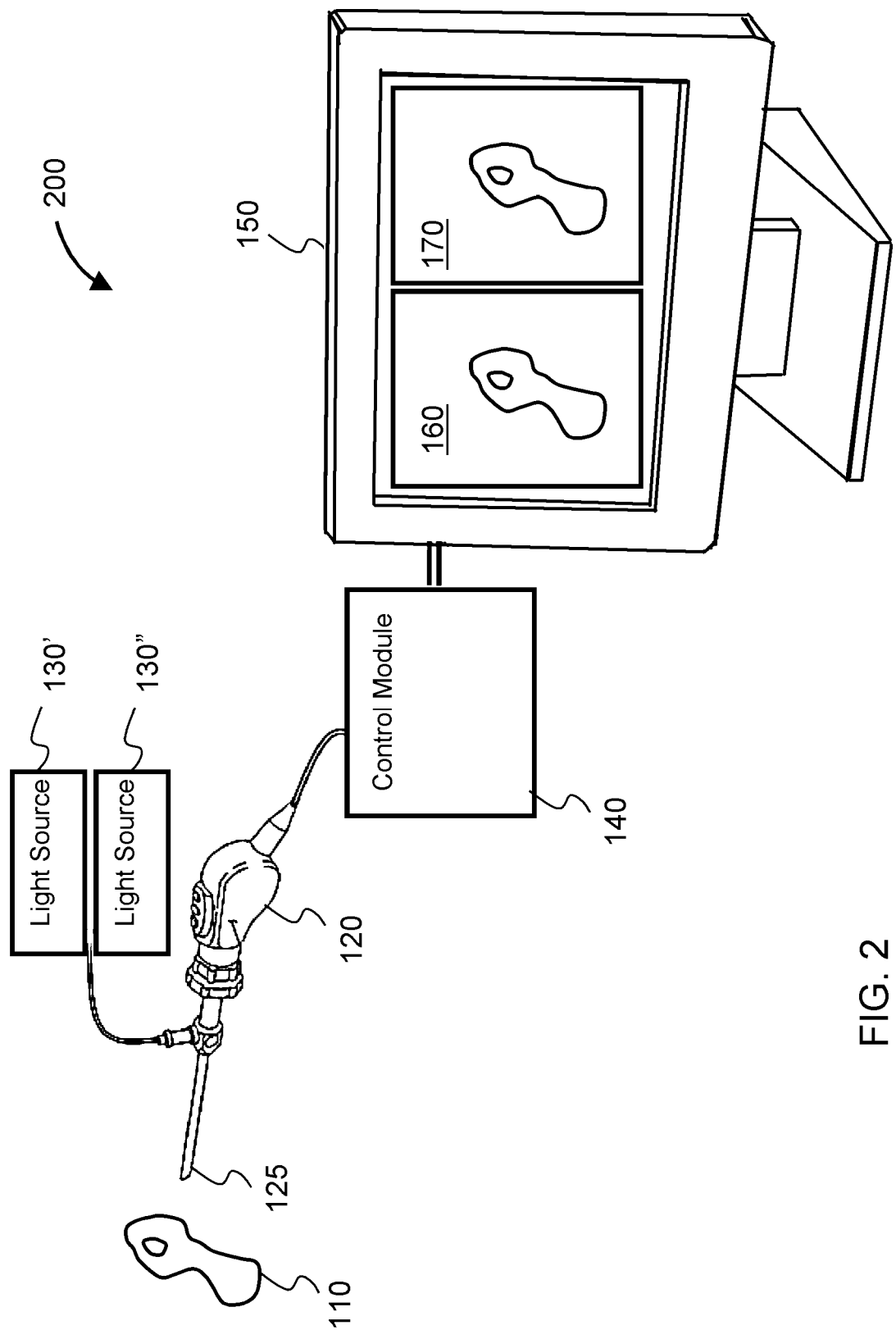
FIG. 2 is a block diagram showing another example system according to aspects of the invention that is a modification of the system shown in FIG. 1.

FIG. 2 shows an example system 200 which illustrates variations on system 100 according to aspects of the invention.

System 200 is substantially identical to system 100 except that light source 130 is replaced with two light sources 130', 130", and images 160, 170 are shown in a side-by-side arrangement on display 150.

The arrangement of images 160, 170 on display 150 may be made arbitrarily in some embodiments.

Using separate light sources 130' 130" may permit design or retrofit of lighting mode arrangements where it is desired to add a light source having different capabilities and/or structure. For example, light source 130' may be a white light producing lamp, and light source 130" may be a laser which produces excitation light in a specific wavelength or wavelength, for example.

Figure 3:
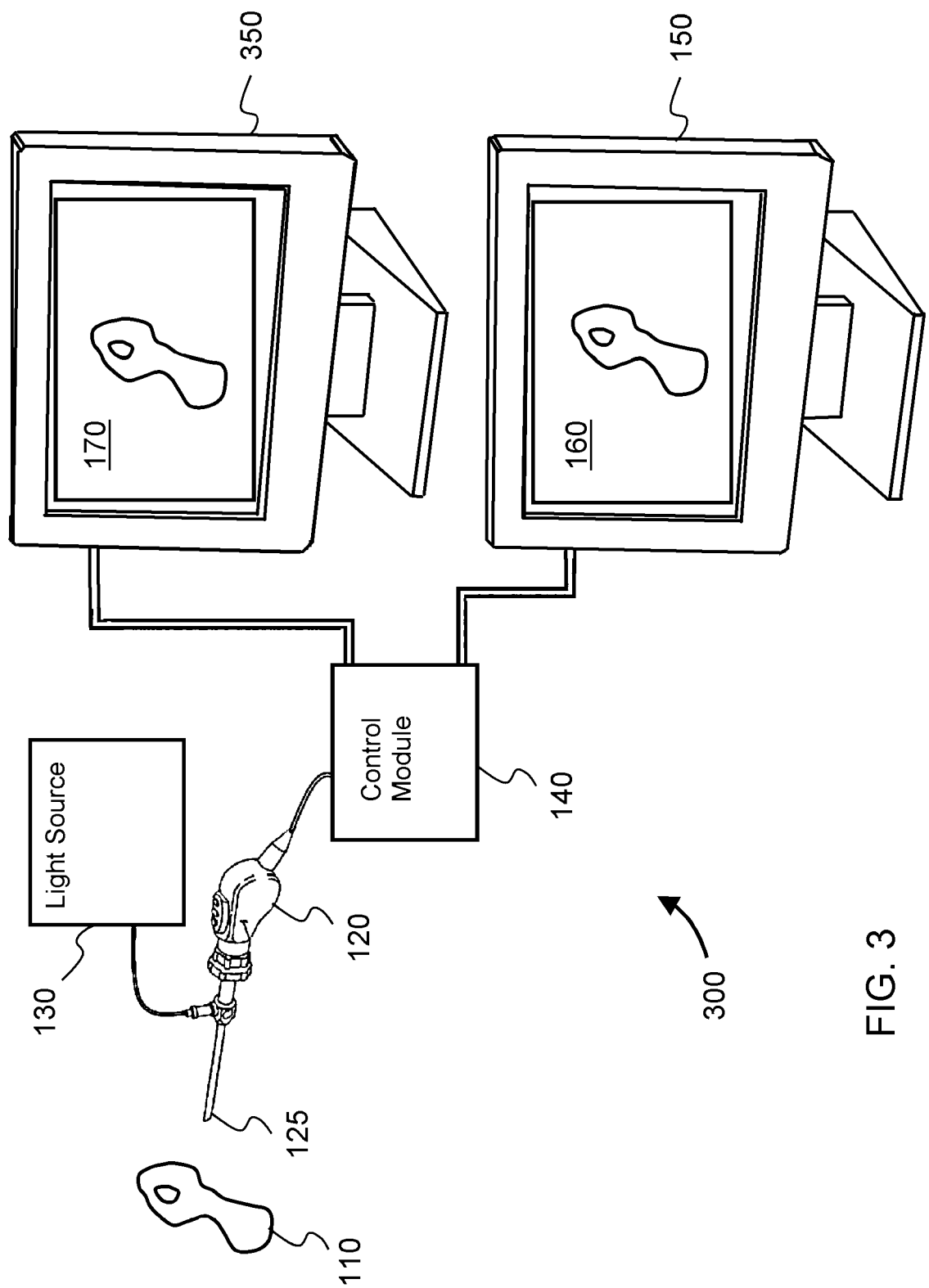
FIG. 3 is a block diagram showing another example system according to aspects of the invention that is a modification of the system shown in FIG. 1.

FIG. 3 shows an example system 300 which illustrates other variations on system 100 according to aspects of the invention.

System 300 is substantially identical to system 100 except that an additional display 350 has been added. In this embodiment, video image 160 is shown on display 150 and still image 170 is shown on display 350.

Using separate monitors in this way can have the advantage of providing larger images and permitting for more efficient workspace management in some embodiments.

Figure 4:
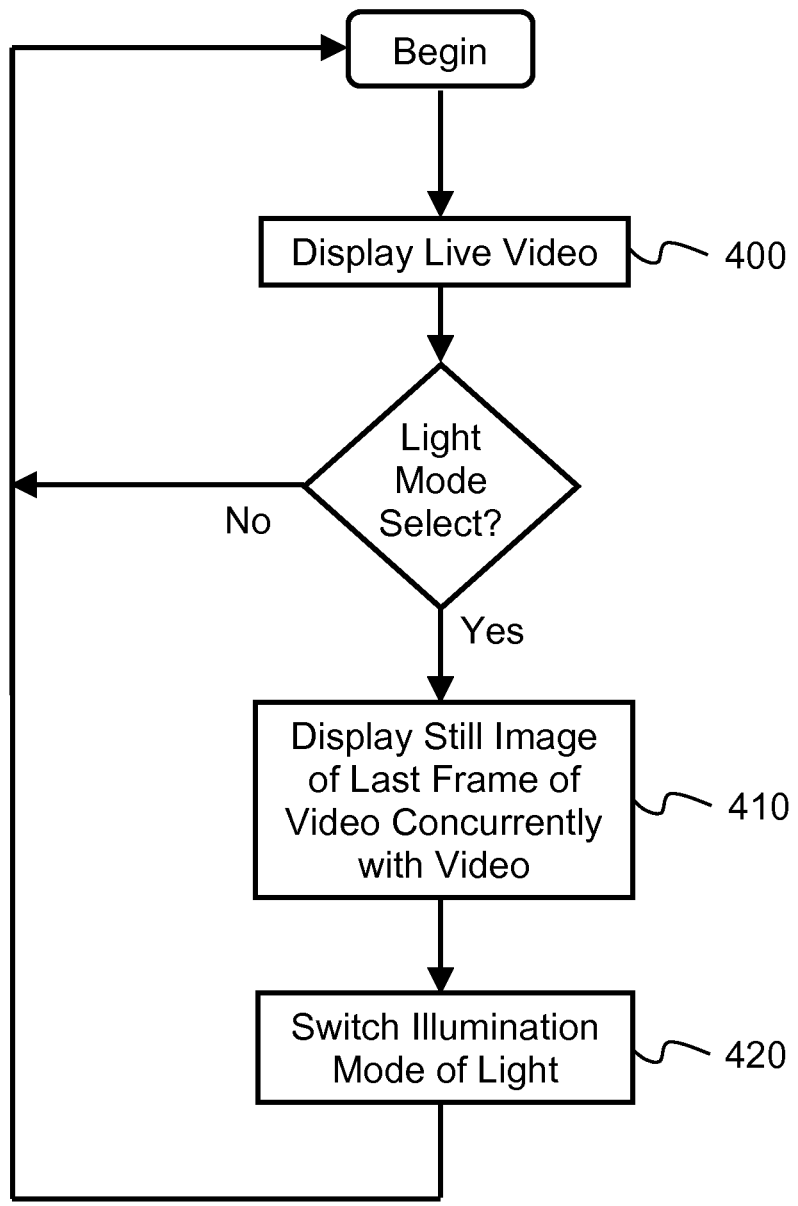
FIG. 4 is a flow chart illustrating operation of the example system shown in FIG. 1.

FIG. 4 is a flow chart which illustrates the operation of systems 100, 200, and 300 according to aspects of the invention.

400: During standard operation, live video is displayed continuously during observation of a procedure, such as an endoscopic surgical procedure for example.

410: If a new mode of operation of the light source or sources is selected, a still image of the most recent frame of video taken under the previous mode of operation is displayed.

420: thereafter, the illumination mode of the light source or sources is switched to the new illumination mode, and display of live video (400) continues under the new illumination mode.

Although the invention has been described with reference to a particular arrangement of parts, features and the like, these are not intended to exhaust all possible arrangements or features, and indeed many modifications and variations will be ascertainable to those of skill in the art.

What is claimed is:

1. An imaging system comprising:
an endoscope;
a first source providing illumination with a first light;
a second source providing illumination with a second light;
an imager capturing video from the endoscope;
a first display area displaying a live video image;
a second display area displaying a still image taken from a frame of the live video image prior to a first change between illumination with the first light and illumination with the second light; and
a control module receiving a user-generated light mode change via a signal from a user control interface for toggling at least between illumination with the first light and illumination with the second light;
wherein, in response to each subsequent change between illumination with the first light and illumination with the second light initiated by the user control interface signal, both the first display area is updated to display a different live video image that is being captured after the respective subsequent change, and the second display area is updated concurrently to display a different still image that is taken from a frame of the live video image prior to the respective subsequent change.

2. The imaging system of claim 1, wherein the first and second sources comprise a single device configured to switch between the first and second lights.

3. The imaging system of claim 1, wherein the first and second sources comprise different devices.

4. The imaging system of claim 1, wherein the second display area is at least partially within the first display area.

5. The imaging system of claim 1, wherein the first display area and the second display area are located on the same display device.

6. The imaging system of claim 1, wherein the first light comprises visible light.

7. The imaging system of claim 1, wherein the second light comprises an excitation light.

8. The imaging system of claim 7, wherein the excitation light comprises at least one wavelength which can activate a fluorescent or photodiagnostic substance.

9. The imaging system of claim 1, wherein the second light comprises non-visible light.

10. An imaging system comprising:

an endoscope;

a first source configured to irradiate an object with a first light;

a second source configured to irradiate an object with a second light;

an imager capturing a video image of said object from the endoscope;

a first display displaying the video image during irradiation with the first light;

a second display displaying a still image taken from a frame of the video image during irradiation with the second light; and a control module receiving a user-generated light mode change via a signal from a user control interface for toggling at least between irradiation with the first light and irradiation with the second light;

wherein, in response to each change between irradiation with the first light and irradiation with the second light initiated by the user control interface signal, both the first display displays a video image that is being captured during a current irradiation with one of the first light or second light, and the second display displays concurrently a still image taken from a frame of the video image during a previous irradiation with the other of the first light or second light.

11. An imaging system comprising:

a control module receiving image information from an endoscope, said image information relating to an object within view of said endoscope, wherein said control module is configured to transmit for display on a first display area a video image of the object, wherein, concurrently with transmitting the video image, said control module is configured to transmit for display a still image that is taken from a frame of the video image prior to a change in wavelength of illumination of the object, wherein said control module is configured to receive a user-generated light mode change via a signal from a user control interface for toggling at least between illumination with a first wavelength and illumination with a second wavelength, wherein, in response to each change in wavelength of illumination initiated by the user control interface signal, the control module is configured to concurrently transmit to the first display area an updated video image of the object being illuminated under a current wavelength, and transmit to the second display area an updated still image taken from a frame of the video image prior to the respective change in wavelength of illumination.

12. The imaging system of claim 1, wherein the user control interface comprises a button.

\* \* \* \* \*